United States Patent [19]

Breddam et al.

[11] Patent Number: 4,579,820

[45] Date of Patent: Apr. 1, 1986

[54] PROCESS FOR ENZYMATIC REPLACEMENT OF THE B-30 AMINO ACID IN INSULINS

[75] Inventors: Klaus Breddam, Glostrup; Jack T. Johansen, Rungsted Kyst, both of Denmark

[73] Assignee: De Forenede Bryggerier A/S, Copenhagen, Denmark

[21] Appl. No.: 458,847

[22] Filed: Jan. 18, 1983

[30] Foreign Application Priority Data

Jan. 22, 1982 [DK] Denmark ............................. 277/82

[51] Int. Cl.$^4$ ..................... C12P 21/04; C12P 21/06
[52] U.S. Cl. ........................................ 435/71; 435/69
[58] Field of Search .................. 435/70, 71, 212, 213, 435/68, 69

[56] References Cited

U.S. PATENT DOCUMENTS

3,276,961 10/1966 Bodanszky ........................... 435/71
4,339,534 7/1982 Johansen et al. ..................... 435/68

OTHER PUBLICATIONS

Breddam, K. et al., *Carlsberg Res. Commun.*, vol. 46(6), p. 361–372, (1981), Chem. Abst. 97:110372h.

Hayashi, R., Bai, Y. and Hata, T.: Further Confirmation of Carboxypeptidase Y as a Metal-Free Enzyme having a Reactive Serine Residue, J. Biochem., 77, 1313–1318, (1975).

Bai, Y. and Hayashi, R.: Properties of the Single Sulfhydryl Group of Carboxypeptidase Y, The Journal of Biological Chemistry, vol. 254, No. 17, Sep. 10, pp. 8473–8479, 1979.

Widmer, F., Johansen, J. T.: Enzymatic Peptide Synthesis Carboxypeptidase Y Catalyzed Formation of Peptide Bonds, Carlsberg Res. Commun., vol. 44, Apr. 23, 1979, 37–46.

Johansen, J. T., Breddam, K., Ottesen, M.: Isolation of Carboxypeptidase Y by Affinity Chromatography, Carlsberg Res. Commun., vol. 41, No. 1, 1976, 1–13.

Breddam, K., Widmer, F., Johansen, J. T.: Carboxypeptidase Y Catalyzed Transpeptidations and Enzymatic Peptide Synthesis, Carlsberg Res. Comm., vol. 45, Nov. 5, 1980, pp. 237–247.

Kubota et al.: Carboxypeptidase $C_N$, J. Biochem., vol. 74, No. 4, (1973), pp. 757–770.

Widmer, F., Breddam, K., Johansen, J. T.: Influence of the Structure of Amino Components on Carboxypeptidase Y Catalyzed Amide Bond Formation, Carlsberg Res. Comm., vol. 46, Apr. 29, 1981, pp. 97–106.

Lee, H. M., Riordan, J. F.: Does Carboxypeptidase Y have Intrinsic Endopeptidase Activity? Biochemical and Biophysical Research Comm., vol. 85, No. 3, 1978, 1135–1142.

*Primary Examiner*—Thomas G. Wiseman
*Assistant Examiner*—Jayme A. Huleatt

[57] ABSTRACT

An insulin such as porcine insulin is reacted enzymatically with an L-amino acid, amide, or ester in the presence of L-specific serine carboxypeptidase modified by reaction with divalent metal ions in aqueous solution or dispersion containing $F^-$, $Cl^-$, $Br^-$, $I^-$, $CN^-$, or $SCN^-$.

18 Claims, No Drawings

PROCESS FOR ENZYMATIC REPLACEMENT OF THE B-30 AMINO ACID IN INSULINS

BACKGROUND OF THE INVENTION

The present invention generally relates to a process for enzymatic replacement of the C-terminal amino acid in the B-chain (B-30) of insulins from various species. In particular the invention relates to the conversion of porcine insulin to human insulin.

In earlier patent applications, e.g. U.S. application Ser. No. 364,856 filed Mar. 23, 1982 and based on International application No. PCT/DK81/00074 published on Feb. 4, 1982 under publication No. WO 82/00301 and European patent application No. 81303383.4 published on Feb. 3, 1982 under No. EP 45187 the applicant has described a general process for the replacement of the B-30 amino acid in insulins by reacting as substrate component the selected insulin with an amine component selected from amino acids, optionally substituted amino acids amides and amino acid esters in the presence of an L-specific serine or thiol carboxypeptidase enzyme in an aqueous solution or dispersion at pH 7 to 10.5. The preferred enzyme is carboxypeptidase Y (CPD-Y) from yeast (*Saccharomyces cerevisiae*) which may advantageously be used for converting porcine insulin (Ins'-Lys-Ala) to human insulin (Ins'-Lys-Thr) by means of a transpeptidation reaction with Thr-NH$_2$.

Depending on the reaction conditions, especially the pH, this process leads directly to human insulin which may contain unreacted porcine insulin or to human insulin amide (Ins'-Lys-Thr-NH$_2$) which may be separated from unreacted porcine insulin by HPLC and subsequently deamidated, preferably by means of CPD-Y. The overall yield in the latter case has been about 20–30%, it being understood that these figures refer to test runs and that optimization of the reaction conditions has not been attempted.

Further details will appear from the above applications the whole contents of which are incorporated herein by reference.

Also the prior art is exhaustively discussed in the above-mentioned applications.

It has now surprisingly been found that the yields previously obtained according to the examples of the above-mentioned applications may be drastically improved by chemical modification of the L-specific serine carboxypeptidase enzymes provided certain reaction conditions are met.

Accordingly, the process according to the invention is characterized by reacting as substrate component the selected insulin Ins-X, wherein X represents the B-30 amino acid, with an amine component selected from the group consisting of (a) L-amino acids of the formula

H—B—OH wherein B is an L-amino acid residue, (b) optionally N-substituted L-amino acid amides of the formula

H—B—NR$^1$R$^2$ wherein B is an L-amino acid residue and R$^1$ and R$^2$ are independently selected from the group consisting of hydrogen, amino, hydroxy, alkyl, cycloalkyl, aryl, heteroaryl and aralkyl or R$^1$ and R$^2$ together with the nitrogen atom form a heterocyclic group which may contain a further hetero atom, and (c) amino acid esters of the formula

H—B—OR$^3$ wherein B is an L-amino acid residue and R$^3$ represents alkyl, cycloalkly, aryl, heteroaryl or aralkyl, in the presence of an L-specific serine carboxypeptidase enzyme which has been chemically modified at the sulfhydryl group by reaction with divalent metal ions in an aqueous solution or dispersion containing at least one of the following ions F$^-$, Cl$^-$, Br$^-$, I$^-$, CN$^-$, SCN$^-$ and having a pH from about 5 to 10.5, thereby to form an insulin derivative.

Ins—B—OH, Ins—B—NR$^1$R$^2$, Ins—B—B—NR$^1$R$^2$ or Ins—B—OR$^3$ or subsequently cleaving a group —NR$^1$R$^2$, —B—NR$^1$R$^2$ or —OR$^3$, if desired.

In a preferred embodiment of the serine carboxypeptidase enzyme is treated with mercuric ions, preferably in the form of HgCl$_2$ in the presence of a suitable buffer. It is a well established fact that carboxypeptidase Y and other serine carboxypeptidases contain an —SH (sulfhydryl) group in the form of a single cysteine residue, vide e.g. Hayashi et al., J. Biochem. 77, 1313–1318 (1975) (Ref. 1) and Bai et al., J. Biol. Chem. 254, 8473–8479 (1979) (Ref. 2) and Widmer et al. (Ref. 7), all being incorporated by reference.

Hayashi et al, investigated the effects of various metal ions on the peptidase and esterase activity of CPD-Y and found that preincubation with Cu$^{++}$, Ag$^+$, Hg$^{++}$, Cu$^+$, Mg$^{++}$, Ca$^{++}$, Ba$^{++}$, Cr$^{++}$, Mn$^{++}$, Fe$^{++}$ and Ni$^{++}$ ion in amounts of 10$^{-4}$ and 10$^{-3}$M resulted in significant losses of peptidase and esterase activities. A particularly significant loss was observed with Hg$^{++}$ (added in the form of HgCl$_2$) which inactivated the enzyme totally. Hayashi et al. assume that the inactivation as far as Hg$^{++}$ is concerned is caused by a blocking of the —SH group.

Bai et al. has further investigated the properties of the —SH group and confirmed the significant decrease in peptidase activity for Hg$^{++}$-treated CPD-Y vs. native CPD-Y on most substrates.

On this basis it would not be expected that a carboxypeptidase Y chemically modified with a divalent metal ion, especially Hg$^{++}$ (CPD-YM) would be capable of catalyzing the conversion of porcine insulin to human insulin amide by transpeptidation with threonine amide.

It was surprisingly found that the use of CPD-YM resulted in a drastic increase in the conversion yield up to 70 to 75% if only the reaction medium also contained halogen ions (F$^-$, Cl$^-$, Br$^-$ and I$^-$) or pseudohalogen ions, e.g. CN$^-$ or SCN$^-$.

Without wishing to be bound by any particular theory it is assumed that the halogen or pseudohalogen ions neutralize the positive charge on the CPD-YM thereby reactivating the inactivated enzyme. However, this mechanism does not explain the drastic yield increase, which will be further illustrated below by way of examples.

The applicable carboxypeptidases in the process of the invention are L-specific serine carboxypeptidases. Such enzymes can be produced by yeast fungi, or they may be of animal, vegetable or microbial origin.

A particularly expedient enzyme is carboxypeptidase Y from yeast fungi (CPD-Y). This enzyme is described in the earlier applications i.a. with reference to Johansen et al. (Ref. 4) who developed a particularly expedient purification method by affinity chromatography on an affinity resin comprising a polymeric resin matrix with coupled benzylsuccinyl groups. CPD-Y has the advantage of having no endopeptidase activity. It is available in large amounts and displays relatively great stability. Further details are given in Refs. 3 and 5.

In addition to CPD-Y, which is the preferred enzyme at present, the process of the invention is feasible with other carboxypeptidases, such as those listed in the following survey:

| Enzyme | Origin Fungi |
|---|---|
| Penicillocarboxypeptidase S-1 | *Penicillium janthinellum* |
| Penicillocarboxypeptidase S-2 | *Penicillium janthinellum* |
| Carboxypeptidase(s) from | *Aspergillus saitoi* |
| Carboxypeptidase(s) from | *Aspergillus oryzae* |
| | Plants |
| Carboxypeptidase(s) C | Orange leaves |
| | Orange Peels |
| Carboxypeptidase $C_N$ | Citrus Natsudaidai Hayata |
| Phaseolain | French bean leaves |
| Carboxypeptidase(s) from | Germinating barley |
| | Germinating cotton plants |
| | Tomatoes |
| | Watermelons |
| | Bromelain(pineapple)powder |

The close relationship between a number of the above carboxypeptidases is discussed by Kubota et al. (Ref. 6).

The process of the invention can in principle be carried out with any natural, semi-synthetic or synthetic insulin as substrate component.

The second participant in the reaction is the so-called amine component which is selected from the group consisting of (a) L-amino acids of the formula

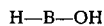
H—B—OH wherein B is an L-amino acid residue, (b) optionally N-substituted L-amino acid amides of the formula

H—B—NR$^1$R$^2$ wherein B is an L-amino acid residue and R$^1$ and R$^2$ are independently selected from the group consisting of hydrogen, amino, hydroxy, alkyl, cycloalkyl, aryl, heteroaryl, and aralkyl or R$^1$ and R$^2$ together with the nitrogen atom form a heterocyclic group which may contain a further hetero atom, and (c) amino acid esters of the formula

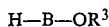
H—B—OR$^3$ wherein B is an L-amino acid residue and R$^3$ represents alkyl, cycloalkyl, aryl, heteroaryl or aralkyl.

The L-amino acid forming part of the amine component may be any of the known L-amino acids, e.g. leu, ile, ala, gly, ser, val, thr, lys, arg, asn, glu, gln, met, phe, tyr, trp or his.

In this context "alkyl" means straight chain or branched alkyl, preferably with 1 to 6 carbon atoms, e.g. methyl, ethyl, propyl, isopropyl, butyl, isobutyl, tert.butyl, amyl, hexyl and the like.

"Cycloalkyl" preferably means $C_3$–$C_8$ cycloalkyl, e.g. cyclopropyl, cyclobutyl, etc.

"Aryl" is preferably phenyl and the like.

"Aralkyl" means benzyl, phenethyl, and the like. As stated the groups R$^1$ and R$^2$ may be the same or different.

"Heteroaryl" as well as the heterocyclic group which may be formed by R$^1$, R$^2$ and the nitrogen atom are represented by e.g. pyridyl, pyrrolidyl, pyrimidinyl, morpholinyl, pyrazinyl, imidazolyl, etc.

All of these groups may be substituted with substituents which are inert with relation to the enzyme, e.g. halo (fluoro, chloro, bromo, iodo), nitro, alkoxy (methoxy, ethoxy, etc.), or alkyl (methyl, ethyl, etc.).

Thus in case of all types of esters the group OR$^3$ is preferably selected from alkoxy groups, such as methoxy, ethoxy or t-butoxy, phenyloxy, and benzyloxy groups. The groups may optionally be substituted with inert substituents, such as nitro groups (p-nitrobenzyloxy).

It is seen that in case of amides, when R$^1$=hydrogen, R$^2$=hydrogen represents the free amide, while R$^2$=OH is a hydroxamic acid, R$^2$=amino is a hydrazide, and R$^2$=phenyl represents an anilide.

As stated in claim 1, the process of the invention is carried out at pH 5.0 to 10.5, preferably at pH 7.0 to 8.5. The preferred pH-value, which is often within a very narrow range, depends upon the pH-optima and pH-minima, respectively, for the different enzymatic activities of the enzyme used.

It should be noted that the operative pH range is broader than when unmodified serine carboxypeptidases are used, since the modification leads to a reduced amidase activity in the range from pH 5 to pH 7, thereby making the isolation of an insulin amide possible even at this range.

If CPD-Y is used as the modified enzyme, the pH-value is preferably 7.0 to 8.5, which is particularly expedient, if an isolation of insulin amide intermediates is desired. At this range of the highest yields of insulin amide are obtained.

The selected pH-value should preferably be maintained throughout the coupling reaction, and may then be changed for precipitation of the reaction products, cleavage of protective groups, etc. A pH might be selected at which the enzyme displays a marked amidase activity whereby the desired insulin is formed in one step. However, preferably a pH is selected where the enzyme displays predominantly peptidase activity thereby favouring the formation of stable insulin amide intermediates, since these may easily be separated from unreacted insulin starting material.

pH-control may be provided by incorporating a suitable buffer for the selected pH-range in the reaction medium, such as a bicarbonate or HEPES buffer.

The pH-value may also be maintained by adding an acid, such as HCl, or a base, such as NaOH, during the reaction. This may conveniently be done by using a pH-stat.

Based on the information given above and in Ref. 3 and 5, the skilled person will be able to select the most suitable reaction conditions, especially with regard to the pH, by which the various enzymatic activities (amidase, peptidase, esterase, carboxypeptidase and peptidyl-amino-acid-amide hydrolase) might best be utilized depending upon the insulin substrate component, the amine component and the intention to suppress or favour the formation of intermediates.

Generally speaking low pH-values within the above range favour the formation and precipitation of an insulin amide intermediate, while higher values lead to a cleaving of the amide group due to the more pronounced amidase activity of the carboxypeptidase enzyme.

However, these conditions may also be influenced upon by varying the enzyme concentration, reaction time, etc.

The reaction is, as mentioned, carried out in a aqueous reaction medium which, if desired, may contain up to 50% by volume of an organic solvent. Preferred organic solvents are alkanols, e.g. methanol and ethanol, glycols, e.g. ethylene glycol or polyethylene glycols, dimethyl formamide, dimethyl sulfoxide, tetrahydrofurane, dioxane and dimethoxyethane.

The selection of the composition of the reaction medium depends particularly upon the solubility, temperature and pH of the reaction components and the insulin products involved and upon the stability of the enzyme.

The reaction medium may also comprise a component that renders the enzyme insoluble, but retains a considerable part of the enzyme activity, such as an ion exchange resin. Alternatively, the enzyme may be immobilized in a manner known per se, cf. Methods of Enzymology, Vol. 44, 1976, e.g. by bonding to a matrix, such as a cross-linked dextran or agarose, or to a silica, polyamide or cellulose, or by encapsulating in polyacrylamide, alginates or fibres. Besides, the enzyme may be modified by chemical means to improve its stability or enzymatic properties.

In case it is desired to suppress any precipitation of insulin amide intermediates, the reaction medium may also contain urea or guanidine hydrochloride in concentrations up to 6 molar. This may also be advantageous at pH-values nd in media where the insulin substrate component has a limited solubility.

The concentration of the two participants in the reaction may vary within wide limits, as explained below. A preferred starting concentration for the insulin substrate component is 0.002 to 0.05 molar and for the amine component 0.05 to 3 molar.

The enzyme concentration may vary as well, but the concentration is preferably $10^{-6}$ to $10^{-4}$ molar, in particular $10^{-5}$ molar. The most advantageous concentration depends i.a. on the substrate concentration, the amine concentration and the reaction time.

As earlier stated the presence of halogen ions (e.g. $F^-$, $Cl^-$, $Br^-$ or $I^-$) or pseudohalogen ions (e.g. $CN^-$ or $SCN^-$) in the reaction medium is decisive for the catalytic effect of the modified enzyme. Thus, the halogen ion concentration depends greatly on the enzyme concentration, at least stoichiometric amounts being necessary, but also on the composition of the reaction medium, the halogen ion in question etc. Generally speaking the concentration may vary from $10^{-4}$ molar to 2 molar.

According to the invention the reaction temperature is preferably 20° to 40° C. The most appropriate reaction temperature for a given synthesis can be determined by experiments, but depends particularly upon the used amine component and enzyme concentration. An appropriate temperature will usually be about 20° to 35° C., preferably about 30° C. At temperatures lower than 20° C. the reaction time will usually be inappropriately long, while temperatures above 40° C. often cause problems with the stability of the enzyme and/or reactants or of the reaction products.

Similar variations occur for the reaction time which depends very much upon the other reaction parameters, especially the enzyme concentration. The standard reaction time in the process of the invention is about 2-6 hours.

It should be added that when using an amide or substituted amide as the amine component, it is normally desired to cleave the amide group specifically from the formed insulin amide. In this respect the unmodified carboxypeptidase, especially CPD-Y is very suitable since CPD-Y exhibits amidase activity at pH>9 while the carboxypeptidase activity is negligible.

Also modified carboxypeptidase might be used, e.g. CPD-Y modified by methyl-Hg or ethyl-Hg. Cleaving with modified enzymes are preferably carried out at pH 7-10 at a temperature of 5° to 35° C.

By the same token the carboxypeptidase might generally be used to cleave the ester groups $OR^3$, as defined from the formed insulin ester intermediate to obtain a final insulin which is not C-terminal protected.

Before the process of the invention will be illustrated by examples, starting materials, methods of measurement, etc. will be explained in general terms.

Starting materials

Porcine insulin was kindly supplied by Nordisk Insulin-laboratorium, Copenhagen. Both highly purified Zn-free insulin, Zn-insulin and crude insulin which had only been purified by citrate crystallization were used. Carboxypeptidase Y from baker's yeast, a commercial preparation of the Carlsberg Breweries, was isolated by a modification of the affinity chromatographic procedure of Johansen et al. (Ref. 4) and obtained as a lyophilized powder (10% enzyme in sodium citrate). Before use the enzyme was desalted on a "Sephadex G-25" column (1.5×25 cm), equilibrated and eluted with water. The concentration of the enzyme was determined spectrophotometrically using $E_{280\ nm}^{1\%} = 14.8$. The enzyme preparation used was free of Protease A as checked by the assay of Lee and Riordan (Ref. 8). L-threonine amide as purchased from Vega-Fox, Arizona, USA. Chromatographic materials were products of Pharmacia, Sweden. All other reagents and solvents were analytical grade from Merck, W. Germany.

Amino Acid Analyses

Samples for amino acid analysis were hydrolyzed in 5.7M HCl at 110° C. in vacuum for 24 hours, and analyzed on a Durrum D-500 amino acid analyzer.

METHODS

HPCL analysis

The conversion of porcine insulin to human insulin amide can be followed by a high pressure liquid chromatography (HPLC) on reverse phase.

A radial-pack $C_8$ column from Waters Ass. was used and elution was achieved with a solution of 0.1M ammonium sulphate containing 30% acetonitrile. Samples (30 µl) from the reaction mixture were diluted with 1M acetic acid before injection into the HPLC.

DISC-PAGE Electrophoresis

The conversion of porcine insulin to human insulin amide can also be followed on DISC-PAGE electrophoresis in 12.5% polyacrylamide gel in a buffer consisting of 0.005M Tris—0.04M Glycine pH 8.3. Human insulin amide migrates slower than porcine insulin corresponding to the loss of one negative charge.

C-Terminal analysis

CPD-Y hydrolysis is used to determine the C-Terminal sequence of the B-chain of insulin. 500 µg insulin in 0.05M MES buffer pH 6.75 is digested with 30 μg CPD-Y at 37° C. for 1 hour. The liberated amino acids are determined on the amino acid analyzer.

Preparative DEAE-Sepharose chromatorgraphy

Human insulin amide is separated from unconverted porcine insulin by ion-exchange chromatography on "DEAE-Sepharose". The lyophilized insulin sample is dissolved in 0.01M Tris—0.05M NaCl—2.5M urea pH 7.5 and applied to the column equilibrated with the same buffer. The insulins are eluted with a NaCl gradient from 0.05 to 0.30M in the same buffer.

Preparation of modified carboxypeptidase Y (CPD-YM)

To 1 ml of an aqueous solution of CPD-Y (9.9 mg/ml (150 μmol)) was added 100 μl 0.5M HEPES pH 7.5 and subsequently 25 μl of an aqueous solution of $10^{-2}$M $HgCl_2$. The preparation was left to stand at room temperature for 10 min. and was then ready for use. Generally stoichiometric amounts of enzyme and mercury are used, but excess of mercury may easily be removed by gel filtration or dialysis. CPD-Y modified with methyl-Hg or ethyl-Hg may be prepared analogously using methyl-HgCl and ethyl-HgCl, respectively.

Test for possible liberation of mercury from CPD-YM

Since the specific esterase activity of native CPD-Y vs. the substrate Bz-Lys-OMe is virtually zero while CPD-YM has a very high activity, this difference may be used to detect a possible liberation of mercury, which would lead to a decrease in esterase activity. However, neither addition of 10 mM EDTA nor gel filtration lead to the slightest decrease in activity, showing that no mercury is liberated.

RESULTS

EXAMPLE 1

80 mg Zn-free insulin was dissolved in 6.5 ml of 1.1M Thr-$NH_2$—0.05M HEPES—1.0 KCl pH 7.0 and 12.7 mg CPD-YM in 2.5 ml 0.05M HEPES pH 7.0 were added. The reaction was carried out at 20° C. and was followed by HPLC and gel electrophoresis. HPLC showed a conversion of 78% after 21 hours of reaction. Gel electrophoresis showed a similarly extensive conversion.

After 21 hours of reaction the pH was adjusted to 2 with 1M HCl and the sample desalted on "Sephadex ®-G50" in 1M—acetic acid and then lyophilized. Chromatography on DEAE-Sepharose showed an elution profile with two peaks. Gel electrophoresis showed that the two peaks were apparently pure. Peak I contained 41.5 mg of human insulin amide. Amino acid analysis of peak I (Table I) showed that alanine was exchanged with threonine. Peak II contained 40% unreacted porcine insulin, which can be used for recycling.

EXAMPLE 2

70 mg crude insulin, citrate crystallized, was dissolved in 2 ml 1.5M Thr-$NH_2$—0.05M HEPES—1.0M HCl pH 7.0. The reaction was performed at 20° C. in the presence of 15 μM CPD-YM. After 72 hours of reaction HPLC showed a conversion of 77%. Gel electrophoresis showed a similar extent of conversion. The reaction mixture was analyzed as described in Example 1. DEAE-Sepharose chromatography showed an elution profile with two peaks in the ratio of 2:1 for human insulin amide and porcine insulin, respectively. Amino acid analysis of Peak I is shown in Table I. Peak II contained 40% unreacted porcine insulin.

TABLE I

| | Amino Acid Analyses of Insulin | | |
|---|---|---|---|
| | Example 1 Zn-free Insulin | | Example 2 Citrate Insulin |
| Amino Acid | Porcine Insulin | Human Insulin amide | Human Insulin amide |
| Aspartic acid | 3.00 | 3.04 | 2.96 |
| Threonine | 1.94 | 3.17 | 3.25 |
| Serine | 2.89 | 2.93 | 2.71 |
| Glutamic acid | 7.05 | 7.03 | 6.90 |
| Proline | 1.17 | 0.77 | 1.10 |
| Glycine | 4.00 | 3.94 | 4.05 |
| Alanine | 2.05 | 1.17 | 1.09 |
| Valine | 3.42 | 3.26 | 3.59 |
| Isoleucine | 1.45 | 1.43 | 1.48 |
| Leucine | 6.02 | 6.23 | 6.24 |
| Tyrosine | 3.76 | 3.72 | 3.78 |
| Phenylalanine | 3.00 | 2.85 | 2.97 |
| Histidine | 1.95 | 2.02 | 2.00 |
| Lysine | 0.99 | 1.00 | 1.00 |
| Arginine | 0.99 | 0.98 | 1.01 |

EXAMPLE 3

100 mg porcine Zn-insulin was dissolved in 6.7 ml 1.0M Thr-$NH_2$, 1M urea, pH 7.5 (pH was adjusted with HBr). 2.3 mg CPD-YM was added. The reaction was carried out at 32° C. and followed by HPLC. After 2 hours 10 min. 75% of the porcine insulin was converted to human insulin amide.

EXAMPLE 4

100 mg porcine Zn-insulin was dissolved in 6.7 ml 1.0M Thr-$NH_2$, 1M urea, pH 8.0 (pH was adjusted with HBr). b 2.7 mg CPD-YM was added. The reaction was carried out at 32° C. and followed by HPLC. After 2 hours 10 min. 73% of the porcine insulin was converted to human insulin amide.

EXAMPLE 5

100 mg porcine Zn-insulin was dissolved in 6.7 ml 1.0M Thr-$NH_2$, 1M urea, pH 8.0 (pH was adjusted with HBr). 3.6 mg CPD-YM was added. The reaction was carried out at 32° C. and followed by HPCL. After 1 hour 40 min. 75% of the porcine insulin was converted to human insulin amide.

EXAMPLE 6

100 mg porcine Zn-insulin was dissolved in 6.7 ml 1.0M Thr-$NH_2$, 1M urea, pH 8.25 (pH was adjusted with HBr). 3.6 mg CPD-YM was added. The reaction was carried out at 32° C. and followed by HPCL. After 1 hour 20 min. 68% of the porcine insulin was converted to human insulin amide.

EXAMPLE 7

100 mg porcine Zn-insulin was dissolved in 6.7 ml 1.0M Thr-$NH_2$, $10^{-4}$M KJ, 1M urea, pH 8.0 (pH was adjusted with $HNO_3$). 3.6 mg CPD-YM was added. The reaction was carried out at 32° C. and followed by HPCL. After 2 hours 5 min. 73% of the porcine insulin was converted to human insulin amide.

EXAMPLE 8

The procedure of Example 3 was repeated except that 3 mg CPD-YM immobilized on silica was used. After 2 hours 75% conversion was obtained.

EXAMPLE 9

The procedure of Example 3 was repeated at the following pH values: 6.5; 6.0; 5.5; 5.0. The following approximate conversions were obtained: 50%, 30%, 20% and 20% human insulin amide.

EXAMPLE 10

The procedure of Example 6 was repeated at pH 8.5. 50% conversion to human insulin amide was obtained.

HPLC, DISC-PAGE and amino acid analysis of the products obtained in the examples showed that they were in fact human insulin amide.

A subsequent deamidation to human insulin may be performed as described in the earlier applications mentioned above.

EXAMPLE 11

Deamidation of human insulin amide with unmodified CPD-Y and modified CPD-Y

A. Unmodified CPD-Y

To a solution of human insulin amide (15 mg/ml) in 1 mM EDTA at pH 8.0, 25° C., is added CPD-Y to a final concentration of 7.2 µM. After 22 min. of reaction 74% of the amide was converted as determined by HPLC. After separation on DEAE-Sepharose, HPLC analysis and amino acid analysis showed that the human insulin was pure.

B. Methyl-Hg modified CPD-Y

As example 11A but with 4.0 µM methyl-Hg-CPD-Y, pH 8.0. After 39 min. of reaction 61% of the insulin amide was converted to human insulin.

C. Ethyl-Hg modified CPD-Y

As example 11A but with 7.2 µM ethyl-Hg-CPD-Y, pH 8.0. After 36 min. of reaction 74% conversion was observed by HPLC.

D. Methyl-Hg modified CPD-Y

As example 11A but with 19 µM methyl-Hg-CPD-Y, pH 7.5. After 2 hours of reaction 90% conversion was observed by HPLC.

REFERENCES b 1. Hayashi, R., Bai, Y. and Hata, T.: Further Confirmation of Carboxypeptidase Y as a Metal-Free Enzyme Having a Reactive Serine Residue, J. Biochem., 77, 1313–1318 (1975).

2. Bai, Y. and Hayashi, R.: Properties of the Single Sulfhydryl Group of Carboxypeptidase Y, The Journal of Biological Chemistry, Vol. 254, no. 17, Sept. 10, pp. 8473–8479, 1979.

3. Widmer, F., Johansen, J. T.: Enzymatic peptide synthesis carboxypeptidase Y catalyzed formation of peptide bonds, Carlsberg Res. Commun, Vol. 44, Apr. 23, 1979, 37–46.

4. Johansen, J. T., Breddam, K., Ottesen, M.: Isolation of carboxypeptidase Y by affinity chromatography, Carlsberg Res. Commun., Vol. 41, No. 1, 1976, 1–13.

5. Breddam, K., Widmer, F., Johansen, J. T.: Carboxypeptidase Y catalyzed transpeptidations and enzymatic peptide synthesis, Carlsberg Res. Comm. Vol. 45, Nov. 5, 1980, p. 237–247.

6. Kubota et al.: Carboxypeptidase $C_N$, J. Biochem., Vol. 74, No. 4 (1973), p. 757–770.

7. Widmer, F., Breddam, K., Johansen, J. T.: Influence of the structure of amino components on Carboxypeptidase Y catalyzed amide bond formation. Carlsberg Res. Comm. Vol. 46, Apr. 29, 1981, p. 97–106.

8. Lee, H.-M., Riordan, J. F.: Does carboxypeptidase Y have intrinsic endopeptidase activity? Biochemical and Biphysical Research Comm., Vol. 85, No. 3, 1978, 1135–1142.

We claim:

1. A process for enzymatic replacement of the B-30 amino acid in insulins, which comprises reacting as substrate component the selected insulin Ins-X, wherein X represents the B-30 amino acid with an amine component selected from the group consisting of L-amino acid amides of the formula $$H—B—NR^1R^2$$

wherein B is an L-amino acid residue and $R^1$ and $R^2$ are independently selected from the group consisting of hydogen, amino, hydroxy, alkyl, cycloalkyl, aryl, heteroaryl and aralkyl or $R^1,N$ and $R^2$ form a heterocyclic ring which may contain an additional hetero atom, and amino acid esters of the formula $$H—B—OR^3$$

wherein B is an L-amino acid residue and $R^3$ represents alkyl, cycloalkyl, aryl, heteroaryl or aralkyl, in the presence of an L-specific serine carboxypeptidase enzyme which has been chemically modified at the sulfhydryl group by reaction with divalent metal ions in an aqueous solution or in a dispersion containing an anion selected from the group consisting of $F^-$, $Cl^-$, $Br^-$, $I^-$, $CN^-$, $SCN^-$ and mixtures thereof and having a pH from about 5 to 10.5, the amount of said anion being at least stoichiometrically equal to that of said enzyme, thereby to form an insulin derivative having the composition Ins—B—$NR^1R^2$, Ins—B—B—$NR^1R^2$ or Ins—B—$Or^3$.

2. The process according to claim 1, wherein the L-specific serine carboxypeptidase enzyme used has been modified by reaction with mercuric ions.

3. The process according to claim 1, wherein the reaction is carried out at pH 7.0 to 8.5.

4. The process according to claim 1, wherein carboxypeptidase Y from yeast is used as the serine carboxypeptidase enzyme.

5. The process according to claim 4, wherein a carboxypeptidase Y is used which has been purified by affinity chromatography on an affinity resin comprising a polymeric resin matrix with a plurality of coupled benzylsuccinyl groups.

6. The process according to claim 1, wherein the L-specific carboxypeptidase enzyme used is selected from the group consisting of penicillocarboxypeptidase S-1 and S-2 from *Penicillium janthinellum*, carboxypeptidases from *Aspergillus saitoi* or *Aspergillus oryzae*, carboxypeptidases C from orange leaves or orange peels, carboxypeptidase $C_N$ from *Citrus natsudaidai Hayata*, phaseolain from french bean leaves and carboxypeptidases from germinating barley, germinating cotton plants, tomatoes, watermelons and Bromelain(pineapple)powder.

7. The process according to claim 1, wherein an immobilized modified L-specific serine carboxypeptidase enzyme is used.

8. The process according to claim 1, wherein an aqueous reaction solution or dispersion containing from 0 to 50% by volume of organic solvent is used.

9. The process according to claim 1, wherein an aqueous solution or dispersion containing urea or guanidine hydrochloride in a concentration of up to 6 molar is used.

10. The process according to claim 1, wherein the concentration of the $F^-$, $Cl^-$, $Br^-$, $I^-$, $CN^-$ or $SCN^-$ is from $10^{-4}$ molar to 2 molar.

11. The process according to claim 1, wherein the substrate component is porcine insulin and the L-amino acid residue in the amine component is a threonine residue.

12. The process according to claim 11, wherein the amine component is threonine amide.

13. The process according to claim 1, wherein an unmodified L-specific serine carboxypeptidase enzyme is used to cleave the group $-NR^1R^2$, $-B-NR^1R^2$ or $-OR^3$.

14. The process according to claim 1, wherein said modified L-specific serine charboxypeptidase enzyme is used to cleave the group $-NR^1R^2$, $-B-NR^1R^2$ or $-OR^3$.

15. The process according to claim 14, wherein the cleaving is carried out at a pH from 7 to 10 at a temperature from 5° to 35° C.

16. The process according to claim 13, wherein the carboxypeptidase enzyme is carboxypeptidase-Y.

17. The process according to claim 14 wherein the carboxypeptidase enzyme is carboxypeptidase-Y.

18. The process according to claim 1 in which the group $-NR^1R^2$, $-B-NR^1R^2$ or $-OR_3$ is subsequently cleaved.

* * * * *

UNITED STATES PATENT OFFICE
CERTIFICATE OF CORRECTION

Patent No. 4,579,820　　　　　　　　Dated April 1, 1986

Inventor(s) Klaus Breddam et al.

It is certified that error appears in the above-identified patent and that said Letters Patent are hereby corrected as shown below:

Column 2, line 20, delete "of";

Column 6, line 40, "as purchased" should be --was purchased--;

Column 8, line 35, "pH 8.0" should be --pH 7.5--;

Column 8, line 36, delete "b" before "2.7 mg";

Column 12, line 4, "carboxypeptidase" is misspelled.

Signed and Sealed this

Fifth Day of August 1986

[SEAL]

Attest:

DONALD J. QUIGG

Attesting Officer　　Commissioner of Patents and Trademarks